(12) United States Patent
Bray

(10) Patent No.: US 7,136,154 B2
(45) Date of Patent: Nov. 14, 2006

(54) DIAMOND CUT SCORING SYSTEM AND METHOD

(76) Inventor: William R. Bray, P.O. Box 8913, Lancaster, PA (US) 17604

( * ) Notice: Subject to any disclaimer, the term of this patent is extended or adjusted under 35 U.S.C. 154(b) by 440 days.

(21) Appl. No.: 10/458,756

(22) Filed: Jun. 9, 2003

(65) Prior Publication Data

US 2004/0051861 A1    Mar. 18, 2004

Related U.S. Application Data

(60) Provisional application No. 60/386,797, filed on Jun. 7, 2002.

(51) Int. Cl.
G01N 21/00    (2006.01)

(52) U.S. Cl. ...................................... 356/30

(58) Field of Classification Search .................. 356/30, 356/445; 702/35
See application file for complete search history.

(56) References Cited

U.S. PATENT DOCUMENTS

| 4,900,147 A | * | 2/1990 | Bowley et al. | ................ 356/30 |
| 5,966,673 A | * | 10/1999 | Shannon, Sr. | ................ 702/35 |
| 6,020,954 A | * | 2/2000 | Aggarwal | ..................... 356/30 |
| 6,813,007 B1 | * | 11/2004 | Lapa et al. | ................... 356/30 |

* cited by examiner

*Primary Examiner*—Layla G. Lauchman
(74) *Attorney, Agent, or Firm*—Charles A. Wilkinson; Clinton H. Wilkinson

(57) ABSTRACT

A gemstone rating system is provided particularly for rating the cut of diamonds in which particular cuts and features are measured and the results compared with and provided with a predetermined score depending upon deviations from a theoretical perfect cut; and wherein the deviation scores are summed and then subtracted from an initially perfect score to provide a universally comparable indication of quality of cut.

12 Claims, 12 Drawing Sheets

Name: 3001569406  Date: 2003/27/03  Time: 09:46:29  Weight: 0.33 ct

| Diameter | 4.45 | 4.43 | 4.46 | 4.42 | 4.45 | 4.43 | 4.46 | 4.42 |
|---|---|---|---|---|---|---|---|---|
| Table % | 0.581 | 0.574 | 0.583 | 0.572 | | | | |
| Crown Deg | 34.2 | 34.4 | 34.3 | 34.4 | 34.7 | 34.4 | 34.6 | 34.2 |
| G.bzl % | 0.036 | 0.041 | 0.034 | 0.038 | 0.038 | 0.041 | 0.034 | 0.041 |
| G.hlv % | 0.038 | 0.041 | 0.038 | 0.041 | 0.038 | 0.038 | 0.043 | 0.041 |
| G.min % | 0.023 | 0.020 | 0.025 | 0.014 | 0.020 | 0.023 | 0.025 | 0.020 |
| | 0.016 | 0.020 | 0.020 | 0.020 | 0.020 | 0.025 | 0.023 | 0.020 |
| Pav Deg | 41.3 | 40.8 | 40.9 | 40.9 | 40.9 | 41.2 | 41.3 | 41.3 |
| Twist Deg | 0.4 | 1.3 | 0.4 | 1.1 | 0.9 | 1.1 | 0.7 | 1.3 |

FIG. 4

| Diameter | 0 | 0 | 0 | 0 | 0 | 0 | 0 | 0 | 0 |
|---|---|---|---|---|---|---|---|---|---|
| Table % | 5 | 0 | 5 | 0 | | | | | 10 |
| Crown Deg | 3 | 1 | 2 | 1 | 2 | 1 | 1 | 3 | 14 |
| G.bzl % | 6 | 8 | 6 | 8 | 8 | 8 | 6 | 8 | 58 |
| G.hlv % | 8 | 8 | 8 | 8 | 8 | 8 | 10 | 8 | 66 |
| G.min % | 4 | 2 | 4 | 2 | 2 | 4 | 4 | 2 | 24 |
| | 2 | 2 | 2 | 2 | 2 | 4 | 4 | 2 | 20 |
| Pav Deg | 12 | 2 | 4 | 4 | 4 | 10 | 12 | 12 | 60 |
| Twist Deg | 0 | 7 | 0 | 7 | 0 | 7 | 0 | 7 | 28 |

Moderation 50%

| Total Deductions | 280 |
|---|---|
| Moderated Deductions | 140 |
| BrayScore | 860 |

FIG. 5

Pavillion Degree Deduction Lookup

| Bottom Main Angle Measurement | Deduction Amount |
|---|---|
| 0 | #N/A |
| 0.1 | #N/A |
| 35.8 | #N/A |
| 35.9 | #N/A |
| 36.0 | #N/A |
| 36.1 | #N/A |
| 36.2 | #N/A |
| 36.3 | #N/A |
| 36.4 | #N/A |
| 36.5 | #N/A |
| 36.6 | #N/A |
| 36.7 | #N/A |
| 36.8 | #N/A |
| 36.9 | #N/A |
| 37.0 | #N/A |
| 37.1 | #N/A |
| 37.2 | #N/A |
| 37.3 | #N/A |
| 37.4 | #N/A |
| 37.5 | #N/A |
| 37.6 | #N/A |
| 37.7 | #N/A |
| 37.8 | #N/A |
| 37.9 | #N/A |
| 38.0 | #N/A |
| 38.1 | #N/A |
| 38.2 | #N/A |
| 38.3 | #N/A |
| 38.4 | #N/A |
| 38.5 | 46 |
| 38.6 | 44 |
| 38.7 | 42 |
| 38.8 | 40 |
| 38.9 | 38 |
| 39.0 | 36 |
| 39.1 | 34 |
| 39.2 | 32 |
| 39.3 | 30 |
| 39.4 | 28 |
| 39.5 | 26 |
| 39.6 | 24 |
| 39.7 | 22 |
| 39.8 | 20 |
| 39.9 | 18 |
| 40.0 | 16 |
| 40.1 | 14 |
| 40.2 | 12 |
| 40.3 | 10 |
| 40.4 | 8 |
| 40.5 | 6 |
| 40.6 | 4 |
| 40.7 | 2 |
| 40.75 | 0 |
| 40.8 | 2 |
| 40.9 | 4 |
| 41.0 | 6 |
| 41.1 | 8 |
| 41.2 | 10 |
| 41.3 | 12 |
| 41.4 | 14 |
| 41.5 | 16 |
| 41.6 | 18 |
| 41.7 | 20 |
| 41.8 | 22 |
| 41.9 | 24 |
| 42.0 | 26 |
| 42.1 | 28 |
| 42.2 | 30 |
| 42.3 | 32 |
| 42.4 | 34 |
| 42.5 | 36 |
| 42.6 | 38 |
| 42.7 | 40 |
| 42.8 | 42 |
| 42.9 | 44 |
| 43.0 | 46 |
| 43.1 | 48 |
| 43.2 | 50 |
| 43.3 | 52 |
| 43.4 | 54 |
| 43.5 | 56 |
| 43.6 | 58 |
| 43.7 | 60 |
| 43.8 | 62 |
| 43.9 | 64 |
| 44.0 | 66 |
| 44.1 | 68 |
| 44.2 | 70 |
| 44.3 | 72 |
| 44.4 | 74 |
| 44.5 | 76 |
| 44.6 | 78 |
| 44.7 | 80 |
| 44.8 | 82 |
| 44.9 | 84 |
| 45.0 | 86 |
| 45.1 | 88 |
| 45.2 | 90 |
| 45.3 | 92 |
| 45.4 | 94 |
| 45.5 | 96 |
| 45.6 | 98 |
| 45.7 | 100 |

FIG. 8

Crown Main Angle Deductions

| Angle | Deduction |
|---|---|
| 29 | 46 |
| 29.1 | 46 |
| 29.2 | 46 |
| 29.3 | 46 |
| 29.4 | 46 |
| 29.5 | 46 |
| 29.6 | 46 |
| 29.7 | 46 |
| 29.8 | 46 |
| 29.9 | 46 |
| 30 | 45 |
| 30.1 | 44 |
| 30.2 | 43 |
| 30.3 | 42 |
| 30.4 | 41 |
| 30.5 | 40 |
| 30.6 | 39 |
| 30.7 | 38 |
| 30.8 | 37 |
| 30.9 | 36 |
| 31.0 | 35 |
| 31.1 | 34 |
| 31.2 | 33 |
| 31.3 | 32 |
| 31.4 | 31 |
| 31.5 | 30 |
| 31.6 | 29 |
| 31.7 | 28 |
| 31.8 | 27 |
| 31.9 | 26 |
| 32.0 | 25 |
| 32.1 | 24 |
| 32.2 | 23 |
| 32.3 | 22 |
| 32.4 | 21 |
| 32.5 | 20 |
| 32.6 | 19 |
| 32.7 | 18 |
| 32.8 | 17 |
| 32.9 | 16 |
| 33.0 | 15 |
| 33.1 | 14 |
| 33.2 | 13 |
| 33.3 | 12 |
| 33.4 | 11 |
| 33.5 | 10 |
| 33.6 | 9 |
| 33.7 | 8 |
| 33.8 | 7 |
| 33.9 | 6 |
| 34.0 | 5 |
| 34.1 | 4 |
| 34.2 | 3 |
| 34.3 | 2 |
| 34.4 | 1 |
| 34.5 | 0 |
| 34.6 | 1 |
| 34.7 | 2 |
| 34.8 | 3 |
| 34.9 | 4 |
| 35.0 | 5 |
| 35.1 | 6 |
| 35.2 | 7 |
| 35.3 | 8 |
| 35.4 | 9 |
| 35.5 | 10 |
| 35.6 | 11 |
| 35.7 | 12 |
| 35.8 | 13 |
| 35.9 | 14 |
| 36.0 | 15 |
| 36.1 | 16 |
| 36.2 | 17 |
| 36.3 | 18 |
| 36.4 | 19 |
| 36.5 | 20 |
| 36.6 | 21 |
| 36.7 | 22 |
| 36.8 | 23 |
| 36.9 | 24 |
| 37.0 | 25 |
| 37.1 | 26 |
| 37.2 | 27 |
| 37.3 | 28 |
| 37.4 | 29 |
| 37.5 | 30 |
| 37.6 | 31 |
| 37.7 | 32 |
| 37.8 | 33 |
| 37.9 | 34 |
| 38.0 | 35 |
| 38.1 | 36 |
| 38.2 | 37 |
| 38.3 | 38 |
| 38.4 | 39 |
| 38.5 | 40 |
| 38.6 | 41 |
| 38.7 | 42 |
| 38.8 | 43 |
| 38.9 | 44 |
| 39.0 | 45 |
| 39.1 | 46 |
| 39.2 | 47 |
| 39.3 | 48 |
| 39.4 | 49 |
| 39.5 | 50 |
| 39.6 | 51 |
| 39.7 | 52 |
| 39.8 | 53 |
| 39.9 | 54 |
| 40 | 55 |

FIG. 9

| G.bzl % | Deduction |
|---|---|
| 0.0% | 4 |
| 0.1% | 4 |
| 0.2% | 4 |
| 0.3% | 4 |
| 0.4% | 4 |
| 0.5% | 4 |
| 0.6% | 4 |
| 0.7% | 4 |
| 0.8% | 4 |
| 0.9% | 4 |
| 1.0% | 4 |
| 1.1% | 4 |
| 1.2% | 4 |
| 1.3% | 4 |
| 1.4% | 4 |
| 1.5% | 4 |
| 1.6% | 4 |
| 1.7% | 4 |
| 1.8% | 0 |
| 1.9% | 0 |
| 2.0% | 0 |
| 2.1% | 0 |
| 2.2% | 0 |
| 2.3% | 0 |
| 2.4% | 0 |
| 2.5% | 0 |
| 2.6% | 0 |
| 2.7% | 4 |
| 2.8% | 4 |
| 2.9% | 4 |
| 3.0% | 4 |
| 3.1% | 4 |
| 3.2% | 4 |
| 3.3% | 6 |
| 3.4% | 6 |
| 3.5% | 6 |
| 3.6% | 6 |
| 3.7% | 6 |
| 3.8% | 8 |
| 3.9% | 8 |
| 4.0% | 8 |
| 4.1% | 8 |
| 4.2% | 8 |
| 4.3% | 10 |
| 4.4% | 10 |
| 4.5% | 10 |
| 4.6% | 10 |
| 4.7% | 10 |
| 4.8% | 12 |
| 4.9% | 12 |
| 5.0% | 12 |
| 5.1% | 12 |
| 5.2% | 12 |
| 5.3% | 14 |
| 5.4% | 14 |
| 5.5% | 14 |
| 5.6% | 14 |
| 5.7% | 14 |
| 5.8% | 16 |
| 5.9% | 16 |
| 6.0% | 16 |
| 6.1% | 16 |
| 6.2% | 16 |
| 6.3% | 18 |
| 6.4% | 18 |
| 6.5% | 18 |
| 6.6% | #N/A |
| 6.7% | #N/A |
| 6.8% | #N/A |
| 6.9% | #N/A |
| 7.0% | #N/A |
| 7.1% | #N/A |
| 7.2% | #N/A |
| 7.3% | #N/A |
| 7.4% | #N/A |
| 7.5% | #N/A |
| 7.6% | #N/A |
| 7.7% | #N/A |
| 7.8% | #N/A |
| 7.9% | #N/A |
| 8.0% | #N/A |

FIG. 10

| Twist Degree | D_duction | | | | |
|---|---|---|---|---|---|
| .0. | 0 | 5 | 35 | 10.1 | 70 |
| 0.1 | 0 | 5.1 | 35 | 102 | 70 |
| 0.2 | 0 | 5.2 | 35 | 10.3 | 70 |
| 0.3 | 0 | 5.3 | 35 | 10.4 | 70 |
| 0.4 | 0 | 5.4 | 35 | 10.5 | 70 |
| 0.5 | 0 | 5.5 | 35 | 10.6 | 70 |
| 0.6 | 0 | 5.6 | 35 | 10.7 | 70 |
| 0.7 | 0 | 5.7 | 35 | 10.8 | 70 |
| 0.8 | 0 | 5.8 | 35 | 10.9 | 70 |
| 0.9 | 0 | 5.9 | 35 | 11 | 77 |
| 1 | 7 | 6 | 42 | 11.1 | 77 |
| 1.1 | 7 | 6.1 | 42 | 11.2 | 77 |
| 1.2 | 7 | 6.2 | 42 | 11.3 | 77 |
| 1.3 | 7 | 6.3 | 42 | 11.4 | 77 |
| 1.4 | 7 | 6.4 | 42 | 11.5 | 77 |
| 1.5 | 7 | 6.5 | 42 | 11.6 | 77 |
| 1.6 | 7 | 66 | 42 | 11 7 | 77 |
| 1.7 | 7 | 6.7 | 42 | 11.8 | 77 |
| 1.8 | 7 | 6.8 | 42 | 11.9 | 77 |
| 1.9 | 7 | 6.9 | 42 | 12 | 84 |
| 2 | 14 | 7 | 49 | 12.1 | 84 |
| 2.1 | 14 | 7.1 | 49 | 12.2 | 84 |
| 2.2 | 14 | 7.2 | 49 | 12.3 | 84 |
| 2.3 | 14 | 7.3 | 49 | 12.4 | 84 |
| 2.4 | 14 | 7.4 | 49 | 12.5 | 84 |
| 2.5 | 14 | 7.5 | 49 | 12.6 | 84 |
| 2.6 | 14 | 7.6 | 49 | 12.7 | 84 |
| 2.7 | 14 | 7.7 | 49 | 12.8 | 84 |
| 2.8 | 14 | 7.8 | 49 | 12.9 | 84 |
| 2.9 | 14 | 7.9 | 49 | 13 | 91 |
| 3 | 21 | 8 | 56 | 13.1 | 91 |
| 3.1 | 21 | 8.1 | 56 | 13.2 | 91 |
| 3.2 | 21 | 8.2 | 56 | 13.3 | 91 |
| 3.3 | 21 | 8.3 | 56 | 13.4 | 91 |
| 3.4 | 21 | 8.4 | 56 | 13.5 | 91 |
| 3.5 | 21 | 8.5 | 56 | 13.6 | 91 |
| 3.6 | 21 | 8.6 | 56 | 137 | 91 |
| 3.7 | 21 | 8.7 | 56 | 13.8 | 91 |
| 3.8 | 21 | 8.8 | 56 | 13.9 | 91 |
| 3.9 | 21 | 8.9 | 56 | 14 | 98 |
| 4 | 28 | 9 | 63 | 14.1 | 98 |
| 4.1 | 28 | 91 | 63 | 14.2 | 98 |
| 4.2 | 28 | 9.2 | 63 | 14.3 | 98 |
| 4.3 | 28 | 9.3 | 63 | 14.4 | 98 |
| 4.4 | 28 | 9.4 | 63 | 14.5 | 98 |
| 4-5 | 28 | 9.5 | 63 | 14.6 | 98 |
| 4.6 | 28 | 9.6 | 63 | 14.7 | 98 |
| 4.7 | 28 | 9.7 | 63 | 14.8 | 98 |
| 4.8 | 28 | 9.8 | 63 | 14.9 | 98 |
| 4.9 | 28 | 9.9 | 63 | 15 | 105 |
| | | 10 | 70 | 15.1 | 105 |

FIG. 11a

| Twist Degree | Deduction |
|---|---|
| 15.2 | 105 |
| 15.3 | 105 |
| 15.4 | 105 |
| 15.5 | 105 |
| 15.6 | 105 |
| 15.7 | 105 |
| 15.8 | 105 |
| 15.9 | 105 |
| 16 | 112 |
| 16.1 | 112 |
| 16.2 | 112 |
| 16.3 | 112 |
| 16.4 | 112 |
| 16.5 | 112 |
| 16.6 | 112 |
| 16.7 | 112 |
| 16.8 | 112 |
| 16.9 | 112 |
| 17 | 119 |
| 17.1 | 119 |
| 17.2 | 119 |
| 17.3 | 119 |
| 17.4 | 119 |
| 17.5 | 119 |
| 17.6 | 119 |
| 17.7 | 119 |
| 17.8 | 119 |
| 17.9 | 119 |
| 18 | 126 |
| 18.1 | 126 |
| 18.2 | 126 |
| 18.3 | 126 |
| 18.4 | 126 |
| 18.5 | 126 |
| 18.6 | 126 |
| 18.7 | 126 |
| 18.8 | 126 |
| 18.9 | 126 |
| 19 | 133 |
| 19.1 | 133 |
| 19.2 | 133 |
| 19.3 | 133 |
| 19.4 | 133 |
| 19.5 | 133 |
| 19.6 | 133 |
| 19.7 | 133 |
| 19.8 | 133 |
| 19.9 | 133 |
| 20 | 140 |
| 20.1 | 140 |
| 20.2 | 140 |
| 20.3 | 140 |
| 20.4 | 140 |
| 20.5 | 140 |
| 20.6 | 140 |
| 20.7 | 140 |
| 20.8 | 140 |
| 20.9 | 140 |
| 21 | 140 |
| 21.1 | 140 |
| 21.2 | 140 |
| 21.3 | 140 |
| 21.4 | 140 |
| 21.5 | 140 |
| 21.6 | 140 |
| 21.7 | 140 |
| 21.8 | 140 |
| 21.9 | 140 |
| 22 | 140 |

FIG. 11b

| G.hv.% | Deduction | | |
|---|---|---|---|
| 0.0% | 4 | 4.4% | 10 |
| 0.1% | 4 | 4.5% | 10 |
| 0.2% | 4 | 4.6% | 10 |
| 0.3% | 4 | 4.7% | 10 |
| 0.4% | 4 | 4.8% | 12 |
| 0.5% | 4 | 4.9% | 12 |
| 0.6% | 4 | 5.0% | 12 |
| 0.7% | 4 | 5.1% | 12 |
| 0.8% | 4 | 5.2% | 12 |
| 0.9% | 4 | 5.3% | 14 |
| 1.0% | 4 | 5.4% | 14 |
| 1.1% | 4 | 5.5% | 14 |
| 1.2% | 4 | 5.6% | 14 |
| 1.3% | 4 | 5.7% | 14 |
| 1.4% | 4 | 5.8% | 16 |
| 1.5% | 4 | 5.9% | 16 |
| 1.6% | 4 | 6.0% | 16 |
| 1.7% | 4 | 6.1% | 16 |
| 1.8% | 0 | 6.2% | 16 |
| 1.9% | 0 | 6.3% | 18 |
| 2.0% | 0 | 6.4% | 18 |
| 2.1% | 0 | 6.5% | 18 |
| 2.2% | 0 | 6.6% | 18 |
| 2.3% | 0 | 6.7% | 18 |
| 2.4% | 0 | 6.8% | #N/A |
| 2.5% | 0 | 6.9% | #NA |
| 2.6% | 0 | 7.0% | #N/A |
| 2.7% | 4 | 71% | #N/A |
| 2.8% | 4 | 7.2% | #N/A |
| 2.9% | 4 | 7.3% | #N/A |
| 3.0% | 4 | 7.4% | #N/A |
| 3.1% | 4 | 7.5% | #N/A |
| 3.2% | 4 | 7.6% | #N/A |
| 3.3% | 6 | 7.7% | #N/A |
| 3.4% | 6 | 7.8% | #N/A |
| 3.5% | 6 | 7.9% | #N/A |
| 3.6% | 6 | 8.0% | #N/A |
| 3.7% | 6 | | |
| 3.8% | 8 | | |
| 3.9% | 8 | | |
| 4.0% | 8 | | |
| 4.1% | 8 | | |
| 4.2% | 8 | | |
| 4.3% | 10 | | |

FIG. 12

| G.min% | Deduction |
|---|---|
| 0.0% | 4 |
| 0.1% | 4 |
| 0.2% | 4 |
| 0.3% | 4 |
| 0.4% | 4 |
| 0.5% | 0 |
| 0.6% | 0 |
| 0.7% | 0 |
| 0.8% | 0 |
| 0.9% | 0 |
| 1.0% | 0 |
| 1.1% | 0 |
| 1.2% | 2 |
| 1.3% | 2 |
| 1.4% | 2 |
| 1.5% | 2 |
| 1.6% | 2 |
| 1.7% | 2 |
| 1.6% | 2 |
| 1.8% | 2 |
| 2.0% | 2 |
| 2.1% | 2 |
| 2.2% | 2 |
| 2.3% | 4 |
| 2.4% | 4 |
| 2.5% | 4 |
| 2.6% | 4 |
| 2.7% | 4 |
| 2.8% | 4 |
| 2.9% | 4 |
| 3.0% | 4 |
| 3.1% | 4 |
| 3.2% | 4 |
| 3.3% | 4 |
| 3.4% | 6 |
| 3.5% | 6 |
| 3.0% | 6 |
| 3.7% | 6 |
| 3.6% | 6 |
| 3.9% | 6 |
| 4.0% | 6 |
| 4.1% | 6 |
| 4.2% | 6 |
| 4.3% | 6 |
| 4.4% | 6 |
| 4.5% | 6 |
| 4.6% | 8 |
| 4.7% | 8 |
| 4.8% | 8 |
| 4.9% | 8 |
| 5.0% | 8 |
| 5.1% | 8 |
| 5.2% | 8 |
| 5.3% | 8 |
| 5.4% | 8 |
| 5.5% | 8 |
| 5.6% | 8 |
| 5.7% | 8 |
| 5.8% | 8 |
| 5.9% | 8 |
| 6.0% | 8 |
| 6.1% | 8 |
| 6.2% | 8 |
| 6.3% | 8 |
| 6.4% | 8 |
| 6.5% | 8 |
| 6.6% | 10 |
| 6.7% | 10 |
| 6.8% | 10 |
| 6.6% | 10 |
| 7.0% | 10 |
| 7.1% | 10 |
| 7.2% | 10 |
| 7.3% | 10 |
| 7.4% | 10 |
| 7.5% | 10 |
| 7.6% | 10 |
| 7.7% | 10 |
| 7.8% | 10 |
| 7.9% | 10 |
| 8.0% | 10 |
| 8.1% | 10 |
| 8.2% | 10 |
| 8.3% | 10 |
| 8.4% | 10 |
| 8.5% | 10 |
| 8.6% | 10 |

FIG. 13

DIAMOND CUT SCORING SYSTEM AND METHOD

This application takes priority from U.S. Provisional Application No. 60/386,797 filed on Jun. 7, 2002, which application is hereby incorporated by reference.

BACKGROUND OF THE INVENTION

1. Field of the Invention

This invention relates to systems for assessing the quality of gemstones such as diamonds, and more particularly to a system and method for grading the cut of a diamond wherein a numerical score indicative of such overall cut quality is calculated for the stone.

2. Preliminary Discussion

Usually, layman diamond purchasers are informed that the cost and value of a diamond is based on the "4 C's"—Clarity, Colour, Cut (proportion), and Carat Weight. The higher grade a diamond receives in each of such categories, the better its overall quality and generally the more costly it will be. Layman diamond purchasers are usually not sufficiently skilled to effectively judge the quality of the cut a diamond. In addition, such quality may be judged differently by different persons despite their experience. Therefore, such purchasing decision is usually based largely upon the carat weight of the diamond, as well as on a visual inspection with the naked eye. Visual inspection is somewhat useful in judging the overall clarity and brilliance of a diamond, although less so to the untrained eye. However, while clarity affects the visual appearance of a diamond, the brilliance of a diamond is primarily but not entirely, influenced by the quality of the cut and proportions of the diamond.

Higher quality diamonds are usually accompanied by an independent grading report or certificate. Grading reports do not include appraisals indicative of the value or worth of a diamond, but rather give an independent expert opinion of the quality of a loose or unset stone. Independent grading reports are available from numerous organizations or labs, the most recognized of which are probably the Gemological Institute of America (GIA) and American Gem Society (AGS), and European Gem Lab (EGL).

The American Gem Society (AGS) certifies professional jewelers as Registered Jewelers (RJ), Certified Gemologists (CG), and Certified Gemologist Appraisers (CGA). In addition, the Grading Reports issued by AGS assigns 0–10 grades to the cut of round diamonds, with 0 being an ideal cut, 1 an excellent cut, 2 a very good cut, 3–4 a good cut, 5–7 a fair cut, and 8–10 a poor cut. Colour and clarity are also rated in a similar manner. The Gemological Institute of America (GIA) also has a scale for rating diamonds that is divided into two categories: colour and clarity. The GIA colour scale grades diamond from D (a total absence of colour) to Z (very deeply coloured). Clarity refers to the number of inclusions (internal marks) and blemishes (external marks) a diamond may have and how visible such marks are. Clarity is graded on a GIA clarity scale which ranges from Fl (flawless) to I-3 (very obvious and potentially damaging marks). GIA's proprietary grading system is well respected and generally considered on par with AGS's scale for color and clarity ratings. However, GIA does not grade cut, so merchants will send stones to AGS for cut scores, particularly if they are confident that the stone will get an AGS 0 or 1 cut score. One drawback of such grading systems is that they do not always consider the inter-relationships between the overall proportions of a diamond, which can significantly effect its appearance. For example, by varying the crown and pavilion angles and table percentage, brilliant diamonds not having "ideal" proportions may result. Research into the interrelationship of factors that contribute to the brilliance of a diamond is continuing.

Other gemological laboratories, such as Harold Weinstein Ltd. (HWL), have developed their own simple cut grading systems. In the HWL system, a stone having ideal proportions is considered an excellent cut and given an HW Grade of 1 to 1+, a good cut stone is given an HW Grade 2 to 3, an average cut is given an HW Grade 4, a commercial cut an HW Grade 5 to 6, and an irregular cut an HW Grade 7 to 8. Other laboratories such as the International Gemological Institute (IGI), Belgium High Diamond Council (HRD), Accredited Gem Appraiser (AGA) and European Gemological Laboratory (EGL) use either similar or individual systems for rating diamonds including the cut of such diamonds.

One drawback of having individual systems for all of such laboratories is that there is not an accepted industry wide standard for cut grading. This encourages dealers to "shop around" to get the most favorable grade or score for a diamond. Dealers are aware of which systems are more liberal with respect to some qualities than others, and therefore will send their stones to such companies depending upon what results they want or need to increase the perceived value of a stone. For example, some reports may have tight grading in the upper qualities but become more liberal as color falls. Another company is known for having well-graded high-grade stones, but for being quite liberal below F grade. Thus, borderline stones are usually sent to "softer" laboratories where dealers are reasonably sure they will receive a more favorable grade or score.

Thus, while there are various systems for individually judging the cut of a brilliant cut diamond, the fact that each laboratory has its own cut grading scale is confusing and leads to inexactness in the marketplace. In addition, none of such known scales is exact enough to be capable of distinguishing between minute differences between stones having closely similar cuts, so that stones having overall significantly different measurements and proportions may be accorded the same basic grade. It is also virtually impossible to accurately and objectively compare the quality of the cut of stones graded by different laboratories. In addition, lower quality stones currently are not typically provided with a grading report, so that many of such stones have less fungability and value than they would if they had a grading report.

3. Description of Related Art

Various devices and arrangements are found in the patented prior art for analyzing crystals and gemstones such as diamonds, although there is little prior art with respect to actual rating or scoring systems for the cut of a diamond. The following references are illustrative of such prior art.

U.S. Pat. No. 1,799,604 issued to F. F. Read entitled "Method and Apparatus for Identifying Crystals" discloses a system wherein a light source is shown upon a diamond, which fragments the light into a plurality of secondary rays. The angles of deflection of the secondary rays are then measured to determine the surface angles of the diamond. Such invention helps identify and distinguish between diamonds that would be considered virtually identical using older identification techniques, but in comparison to today's electronic measurement machines provides only a limited amount of information about the diamonds. In addition, the angles measured are not applied to a grading scale similar to the present inventor's grading system.

U.S. Pat. No. 4,125,770 issued to A. R. Lang entitled "Diamond Identification" teaches a technique for identifying gem quality diamonds in both a rough as well as a cut state wherein the topographical characteristics and internal defects of the stone that are not changed during cutting are analyzed using x-ray topography to measure x-ray diffraction at the "Bragg angle." Lang does not attempt to grade or score the quality of the cut of a diamond, however.

U.S. Pat. No. 4,259,011 issued to J. C. Crumm et al. entitled "Optical Gem Analyzer" discloses an optical gem analyzing machine wherein the gem is irradiated with wide spectrum light and measurements are taken of the reflection and refraction angles of the light passing through the gem. The resulting measurements are then compared with known reference readings, and the quality of the cut is estimated based on the amount of deviation from such reference readings. No system or method applying such measured results to an overall numerical scale as in the present inventor's system is shown, however.

U.S. Pat. No. 4,291,975 issued to P. M. Raccah entitled "Apparatus for Determining the Color Characteristics of a Gem" discloses a device for measuring the color characteristics of a gem whereby the spectral distribution of light passed through the stone is measured and then compared against and graded using the Gemological Institute of America (GIA) color standard. Raccah teaches an apparatus for measuring gem color, rather than cut, and does not teach a new system for grading or rating either the color or cut quality of a diamond.

U.S. Pat. No. 4,482,245 issued to H. Makabe et al. entitled "Apparatus for Measuring the Color of a Brilliant-Cut Diamond," discloses another apparatus for measuring the color of a diamond using a monochromator to analyze the spectrum of light passed through the diamond. The color measurements are then compared with standard GIA or International Confederation of Jewelry, Silverware, Diamonds, Pearls and Stones (C.I.B.J.O.) measurements to determine a color grade. Therefore, Makabke et al. does not teach a new grading system but rather another apparatus for analyzing a gem. Numerous other color measuring devices are known in the prior art.

U.S. Pat. No. 4,875,771 issued to H. J. Bowley entitled "Method for Assessing Diamond Quality" discloses a method wherein a laser Raman spectrometer calibrated to known diamond characteristics is used to determine the qualities of a diamond. Essentially a laser beam is directed at the diamond, and the intensity of the resulting scattered Raman radiation spectrum is compared with standard intensities. U.S. Pat. No. 4,900,147 also issued to H. J. Bowley entitled "Diamond Mapping" discloses a similar method wherein the intensity of Raman radiation is used to map the crystalline structure of a diamond. In addition, U.S. Pat. No. 4,907,875 also issued to H. J. Bowley et al. entitled "Diamond Separation Process," discloses a diamond color assessment apparatus which measures Raman radiation wavelengths. A simple color rating system based on measured Raman wavelengths is disclosed in this reference; however, none of the Bowley et al. references teaches a grading scale similar to that of the present inventor used to rate the quality of the cut of a brilliant cut diamond.

U.S. Pat. No. 5,424,803 issued to D. Andrechuk entitled "Method and Apparatus for Determining the Facet Angles of a Gemstone," discloses an apparatus that measures the angle of light reflected off of each facet of a gemstone when compared to a scale having angular measurement indicia thereon. Such information is indicative of the quality of a stone, particularly a diamond; however, Andrechuk does not teach a system for taking such information and using it to assign a quality grade or score to the stone, which is the basic method of the present invention.

U.S. Pat. No. 5,615,005 issued to K. A. Valente et al. entitled "Gemstone Evaluation System," discloses an apparatus for evaluating primarily the color quality of gemstones using optical evaluation techniques. The gemstone is placed in a spherical analysis chamber and the wavelengths of light are passed through the gem and measured. Such information is digitized so that a computer program can compare the readings with standard readings for each pixel of data, and then for the gemstone as a whole. Images of such stones may also be taken and provided to prospective buyers, thereby decreasing the likelihood of return of the stone after actual inspection by such prospective buyer.

U.S. Pat. No. 5,950,178 issued to S. Borgato entitled "Data Processing System and Method for Facilitating Transactions in Diamonds" discloses a system for bringing together buyers and sellers of diamonds and facilitating diamonds sales between such parties. To facilitate such transactions, information concerning the quality and characteristics of diamonds is input into a computer system and displayed to prospective buyers and sellers. The diamonds may be categorized by weight class, cut depending upon the shape, or other parameters. Borgato does not teach a system for grading the overall quality of the cut of a brilliant cut diamond, however.

U.S. Pat. No. 5,966,673 issued to P. T. Shannon, Sr. entitled "System and Method for Computerized Evaluation of Gemstones" discloses a system for grading the cut of a gemstone wherein a three-dimensional profile of the stone is generated, rather than a two-dimensional model as with the two-dimensional profile of the standard Tolkowsky cut. The basic steps in the Shannon, Sr. method are building a data model of the gemstone, illuminating the stone with an illumination model, tracing the propagation of light within and exiting the stone, determining the light exiting the stone, and grading the stone based on such exiting light. Shannon, Sr. is directly primarily directed to a new cut analysis and measuring technique and machine, rather than a new cut grading system. However, such reference states that the grade may be an average, weighted sum, or other expression, and is a composite cut grade.

U.S. Pat. No. 6,020,954 issued to L. K. Aggarwal entitled "Method and Associated Apparatus for the Standardized Grading of Gemstones" discloses a method wherein a comprehensive analysis of the color, cut, clarity and other qualities of a gemstone is provided via a charge coupled device (CCD) camera, thereby claiming to provide more consistency between grading measurements. While the Aggarwal measuring and grading apparatus is one of the more comprehensive systems for analyzing a gemstone in the prior art, it still does not disclose a new or different rating system for generating a comprehensive single numerical score that may be used to evaluate or compare the quality of such diamonds.

Significant advances in the tools used to measure the accuracy of the cut and proportions of a diamond have been made in recent years. Although diamonds used to be graded for cut mostly by visual estimation, today there are several electronic machines available that analyze and determine the angles and proportion of the cuts. The most popular of these machines are manufactured by Sarin Technologies, Ltd. of Israel and having a U.S. office in New York, N.Y. The Sarin DiaScan and DiaMension machines are capable of more precisely measuring the facet angles and proportions of a cut diamond. The American Gem Society (AGS) uses the Sarin DiaScan machine to measure the proportions of diamonds in producing a grading report as well as in establishing its ideal cut standard. The DiaScan machine essentially measures facet inclinations by plotting interceptions using computerized machine vision and advanced 3D image processing, and provides consistently repeatable proportion measurements of round and fancy gemstones based on proportion measurements of international laboratories to an accuracy of ±0.2 degrees. Reports with such measurements are then generated and available for analysis. With the advent of such electronic measuring devices, which have now become standard in the industry, there is a need for a standardized grading diamond cut grading system that is accurate and objective and which assigns an overall cut quality grade or score to a diamond that is indicative of the quality of cut of such diamond and which is capable of distinguishing between minute differences in the cut of two stones. The present inventor with his cut grading system and method fulfills such need.

OBJECTS OF THE INVENTION

It is a primary object of the invention to provide a single system and method for accurately and objectively estimating the overall quality of the cut of a diamond.

It is a further object of the invention to provide a system and method for accurately and objectively estimating the overall quality of the cut of a diamond that may be used by any laboratory, shop, individual, or organization and can also identify any particular mistakes made by the cutter.

It a still further object of the invention to provide a system and method for calculating a comprehensive numerical score that is indicative of the overall quality of the cut of a brilliant cut diamond, which score not only conveys information about the quality of the cut of such diamond but may also be used to objectively compare such cut with the quality of the cut of another diamond which has been assigned a score using such system.

It is a further object of the invention to provide a system and method that immediately conveys to both the layman diamond purchaser and diamond industry professionals objective and accurate information about the overall quality of the cut and workmanship of a diamond, which information is obtained simply by referring to a single numerical score.

It is a still further object of the invention to provide a system and method which would allow a layman diamond purchaser to quickly, simply and objectively compare the quality of the cut and workmanship of one diamond with the quality of the cut and workmanship of one or more other diamonds.

It is a still further object of the invention to provide a software program for calculating a numerical score evidencing the overall quality of the cut of a diamond based on measured values commonly used as criteria for evaluating the cut of a diamond.

It is a still further object of the invention to provide a software program for assigning a single score to the cut of a diamond wherein data is electronically transmitted to the software platform, and a single score is transmitted electronically back to the sender of the score.

It is a still further object of the invention to provide a computer program such that when the measured values related to the quality of cut of the diamond are input into the program, a comprehensive numerical value is generated.

It is a still further object of the invention to provide an Internet-based platform for automatically receiving and analyzing score information and then calculating and delivering a stone score to a customer, as well as for verifying the score of a previously analyzed and rated diamond.

It is a still further object of the invention to provide a system and method for estimating the overall quality of the cut of a diamond having the potential to fuel growth in all sectors of the diamond trade industry, including the market that buys and sells lower clarity grade stones that presently are not graded, thereby enabling a secondary diamond market to be established based on such system.

Further objects, features, and advantages of the present invention will be more fully appreciated by reference to the following detailed description of one or more presently preferred, but nonetheless illustrative, embodiments in accordance with the present invention.

SUMMARY OF THE INVENTION

A system for assessing the overall quality of the cut of gemstones such as brilliant cut diamonds wherein an overall numerical score or value indicative of such quality is calculated for each diamond. Such system allows persons with limited knowledge of diamonds and how to evaluate, judge, or compare the cut quality of one or more diamonds to do so simply by comparing the numerical scores or grades of such diamonds. A plurality of measurements related to the cut of each diamond will be used. In one preferred embodiment, the angle, straightness, and depth of the top or crown main facets, bottom main or pavilion facets, and top and bottom brilliandeering facets are measured, and the straightness and angle of the star facets is measured. In addition, the table and "out of roundness" of each diamond is measured, and the center of girdle line from which depth measurements of the diamond are taken is determined. The overall polish of the stone may also be subjectively judged.

The calculation of a numerical score for each diamond is based on a plurality of Deduction Rules defined by the inventor's system for the individual measurements. In the preferred embodiment, each diamond starts with a perfect score value such as 1000. Following such Deduction Rules, points will be deducted for all mistakes or deviations from desirable cutting measurements. Measurements are preferably taken from an electronic measuring machine such as the DiaScan machine manufactured by Sarin Technologies. A computer program is provided to facilitate making the required calculations, computations, and deductions, although the system may also be implemented manually. The present system and method also preferably may be utilized via an electronic network such as the Internet, wherein the user will log into an Internet site and input his or her cut measurements, after which a cut grade or score in accordance with the present invention will be generated. Verification of a previously calculated score for a diamond may also be obtained over the Internet. After the required measurements have been taken and deductions assigned to each deviation, such deductions are summed up and subtracted from the perfect score value of 1000. An abbreviated scoring system and method is also described, and a scaling factor is preferably used to standardize or moderate the resulting scores between the two systems. A comprehensive, accurate scoring or grading system that is indicative of the overall quality and workmanship of the cut of each diamond results. Such scores may then be compared, thereby serving as a quick and simple guide for comparing the overall quality of any diamonds having been assessed and assigned a numerical score. While there are known diamond classification systems that utilize ranges of numbers to individually indicate the four basic aspects of each diamond, which systems are useful for their own purposes, they are much less accurate than the present inventor's systems, and do not result in a comprehensive, easily understandable score or numerical value that allows the overall quality of the cut or workmanship of all aspects of diamonds to be easily and quickly compared. The present system and method therefore represents a significant advance of such previous systems. The present inventor's system may also be accomplished using a software program incorporated into currently existing cutting or analysis machines.

BRIEF DESCRIPTION OF THE DRAWINGS

FIG. 4 is a representation of sample data from a DiaScan measurement report.

FIG. 5 is a report showing the applicable point deductions taken based on the Deduction Rules of the second described embodiment of the invention and using the data shown in DiaScan report in FIG. 4.

FIG. 8 illustrates the Bottom Main Facet Angle degree lookup table supporting the Bottom Main Facet Angle Deduction Rule in the first preferred embodiment of the invention.

FIG. 9 illustrates the Crown Main Facet Angle Lookup Table having the deduction point values for the Top Main Facet supporting the Top or Crown Main Facet Angle Deduction Rule in the first preferred embodiment of the invention.

FIG. 10 illustrates the G.Bzl % Deduction lookup table having the deduction point values for the Bottom Main Facet Depth Deduction Rule.

FIG. 11 illustrates the Twist Degree lookup table supporting the Bottom/Top Brilliandeering Facet Straightness Deduction Rule.

FIG. 12 illustrates the G.hlv % Deduction lookup table supporting the Bottom/Top Brilliandeering Facet Angle Deduction Rule.

FIG. 13 illustrates the G.min % Deduction lookup table supporting the Bottom/Top Depth Deduction Rule.

DETAILED DESCRIPTION OF THE PREFERRED EMBODIMENTS

Figure 1:
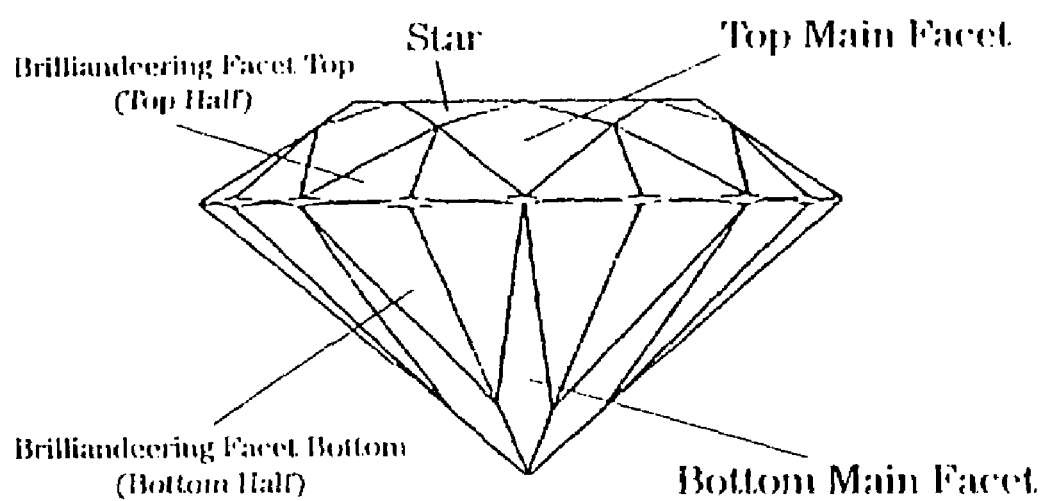
FIG. 1 is a representation of a brilliant cut diamond with the major facets labeled and identified.

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention.

In its broadest aspect, the invention is directed to a unique system and method which enables interested persons to quickly assess and compare the quality and workmanship of the cut of gemstones such as brilliant cut diamonds. The term "cut" actually refers to the geometric proportions of the gem. The geometric proportions of a diamond are critical, since the diamond acts as a prism that refracts, or bends, light rays entering from the top of the diamond. These light rays are funneled downward and strike the plurality of facets along the bottom or pavilion of the diamond. The rays are broken into single colors and are refracted upwardly to the other facets of the stone several times, finally exiting the stone at the top. The amount of refraction of light in a diamond is a factor in giving such diamond its brilliance.

The modern round brilliant cut diamond cut has a total of 57 facets, or 58 if there is a culet. For purposes of reference and review, and since the various facets of such diamond are referred to repeatedly below in describing the inventor's system, the standard terms used in referring to the facets and portions of a brilliant cut diamond are defined generally below. In addition, FIG. 1 visually illustrates a brilliant cut diamond with the parts being labeled.

Angle: the angle of the facets with respect to the Girdle.

Bottom Main Facet: also called Pavilion Main Facet; these are the eight facets extending from the Culet or point of the diamond to the lower Girdle.

Crown: the top portion of the diamond, i.e. the part above the girdle. The Crown consists of a large octagonal facet on top of the diamond called a Table; eight downwardly pointing triangular facets called Star Facets; eight Top Main Facets or Bezel Facets having a kite-shape extending from the table corners to the edge of the girdle; and sixteen Upper Brilliandeering or Upper-Girdle Facets arranged in pairs and encircling the lower crown portion adjacent the Girdle.

Culet: the small facet or cut at the bottom of a full-cut diamond. The culet is meant to flatten the bottom point so that the diamond is not as vulnerable to chipping. If the culet is not present, or is too small, the stone will chip more easily. If the bottom of the diamond is pointed, it is considered to not have a culet.

Girdle: the outer edge of a stone located between the upper and lower or Crown and Pavilion portions.

Lower Brilliandeering Facet: also called Lower Girdle Facet; one of sixteen facets extending along the lower Girdle pointed downwardly and arranged in pairs.

Pavilion: the lower or bottom portion of a diamond below the Girdle. The Pavilion may include a Culet, a small facet at the bottom of the lower portion. The Pavilion also includes eight kite-shaped facets extending from the Culet to the lower Girdle called Pavilion or Bottom Main Facets; and sixteen Lower Brilliandeering or Lower-Girdle Facets arranged in pairs and encircling the upper Pavilion portion adjacent the Girdle.

Star Facet: one of eight downwardly pointing triangular facets on the upper Crown portion of the diamond adjacent the Table.

Table: the large facet situated on top of the Crown of the diamond.

Top Main Facet: Also called Bezel Facets; the eight large kite-shaped facets on the Crown portion.

Upper Brilliandeering Facets: Also called Upper-Girdle Facets; the sixteen facets found in pairs on the lower Crown portion adjacent the girdle.

Although not necessarily immediately evident upon visual inspection with the naked eye, many stone cuts lack proper proportion and refraction of light. As an example, the cut may be too heavy or too deep, wherein instead of being refracted, light escapes through the lower pavilion. On the other hand, if the cut is too shallow, light rays will leak away at the bottom. The bottom main facet or pavilion angle is often considered the most important angle, since rays of light should bounce off at least two pavilion facets, whereas crown facets bend only some rays as they enter or leave. In addition, too much weight above or below the girdle will affect the stone's brilliance and/or fire. As another example, if the girdle, which is where the setting holds the stone, is too thin, the diamond may chip there, while if the girdle is unevenly cut, the stone will be problematic to set.

While electronic machines for quickly and accurately measuring the angles and proportions of gemstones such as diamonds are now available, such as the DiaScan machine manufactured by Sarin Technologies Ltd. of Israel, there remains a need for an easily understood and usable system for grading or scoring the cut of brilliant round diamonds based on these measurements. The present inventor's system and method, which is preferably implemented electronically in the form of computer software or a computer program but which may also be implemented manually, fulfills this need. This inventor's system and method utilizes the measurements taken of the cut of a diamond and applies a series of Deduction Rules to such measurements, with point deductions taken for each cutting "mistake" or deviation from a desirable measurement as defined by the Deduction Rules. In its fullest form, measurements of the cut of each facet of the stone, including the Table, as well as of the Girdle and overall roundness of the brilliant cut stone are assessed in calculating a cut quality score. While two preferred embodiments of the system and method are discussed in detail below, it should be evident that a number variations of such system and method fall within the scope of the claims of the invention, and that the invention is by no means restricted to such embodiments.

The resulting scoring system provides a means for quickly and simply assessing the cut quality of a given brilliant cut diamond, and provides a basis for comparing such cut quality with another brilliant cut diamond scoring higher or lower. The present inventor's system and method relies on exact measurements, rather than extrapolations of measurements used in other systems. In addition, the present system is so accurate it can account for minute cut differences between diamonds having no visible differences and which might otherwise go unnoticed and are not considered by other systems.

Numerous other benefits may depend from having a single cut scoring system, such as increasing the fungability of diamonds on the open market, possibly serving as a basis for trading of diamonds on the commodity exchange, encouraging cutters to make more precise cuts, adding value to premium cut stones by better differentiating them from slightly lesser stones, and adding value to lower clarity stones if a score is applied to them, also by differentiating them from other stones. Therefore, the present system may benefit the entire diamond industry, including dealers, retailers, laboratories, manufacturers, and retail consumers, and may also be used in price guide sheets to improve the accuracy of diamond pricing.

Practice of the present invention is described below with reference to flowcharts, tables, diagrams, and illustrations of methods, systems, and computer program products according to the embodiments of the present invention. It will be understood that where appropriate or required each block of the block diagrams or tables, and/or flowcharts illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create structures for implementing the functions specified in the block diagram and/or flowchart block or blocks and tables.

These computer instructions may also be stored in computer readable memory that can direct a computer or other programmable data processing apparatus to function in a particular manner, such that the instructions stored in the computer readable memory produce an article of manufacture including instructions which implement the function specified in the flowchart block or blocks, tables, and/or in the block diagram. The computer readable instructions may also be loaded on a computer of other programmable data processing apparatus to produce a computer implemented process or method such that the instructions which execute on the computer or other programmable apparatus provide steps for implementing the functions specified in the block diagram and/or flowchart block or blocks.

The sequence of cut analysis of the invention as described below is based on the actual cutter's methodology and sequence of cutting or placing facets on a diamond, although such sequence may be altered where possible without affecting the working of the present system and method. Referring now to FIG. 1, for purposes of clarity there is illustrated a brilliant cut diamond having the typical number of fifty-seven facets on its surface, not including the Culet. More particularly, a standard brilliant cut diamond as shown in FIG. 1 is comprised generally of a top section or Crown and a lower section or Pavilion, which sections are separated by a Girdle. The Crown is comprised of a large octagonal Table (not shown), eight downwardly-pointing Star Facets surrounding the Table, eight Top Main Facets extending from the Table to the Girdle, and sixteen Top Brilliandeering Facets arranged in pairs around the perimeter of the Crown. Below the Girdle is the lower section or Pavilion, which is comprised of eight Bottom Main Facets extending from the end or Culet (if present) to the Girdle, and sixteen Lower Brilliandeering Facets arranged in pairs immediately below the Top Brilliandeering Facets.

In the embodiments described below, all measurements are obtained using an electronic measuring machine. The first embodiment described is based on full capability technology, while the second embodiment is based on measurements taking using the Sarin DiaScan electronic measuring apparatus or a similar electronic measuring device. The preferred computer requirements for use of the DiaScan machine according to Sarin Technologies are a computer system having a Pentium-III 500 MHz or higher processor, 128 MB RAM or higher, a CD-ROM drive, a 17" graphics display monitor, and using the Windows 98/2000/XP operating system. In addition, while the invention as described below includes a detailed description of the measurements required in the present inventor's scoring system and method, it should be understood that such measurements may have been previously computed, particularly in the second embodiment, in which case the measurements will simply either be input into the computer software program of the invention, whereby the program will carry out the appropriate instructions in calculating a score, or such calculations can be made manually.

Center of Girdle Line

Figure 2:
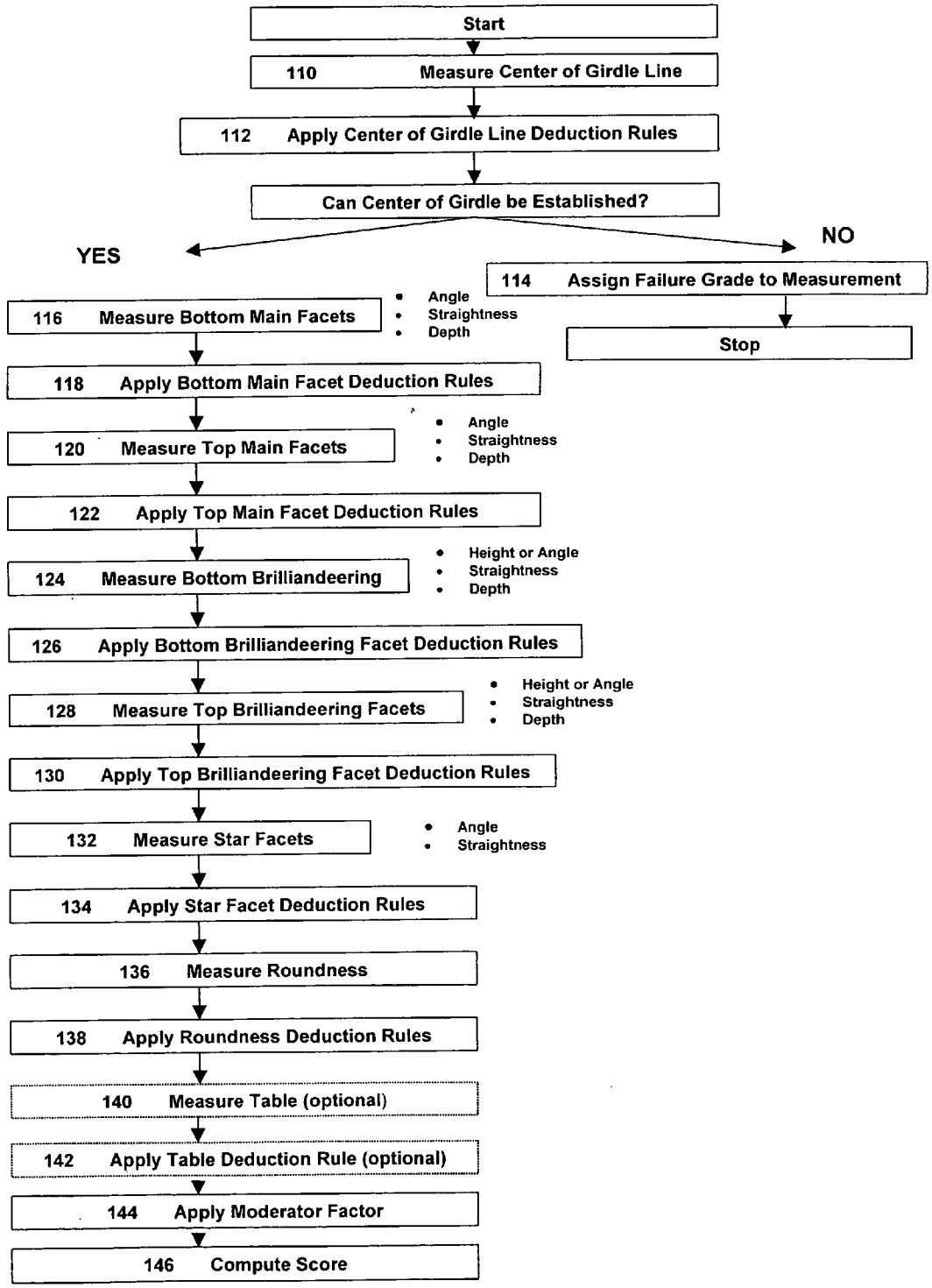
FIG. 2 is a flow chart of steps in measuring and assessing the quality of the cut of a diamond in the first described embodiment of the invention.

FIG. 2 is a flow chart showing the basic steps in measuring and assessing such measurements using the Deduction Rules of the system and method of the invention. In the first described embodiment of the invention, the initial measurement (Step 110) to be taken is of the Center of Girdle Line of the stone. This line is an imaginary line that is derived by averaging two measurements. The first averaged measurement is of a minimum of eight measurements taken from the Table of the diamond to the center point at the Girdle of a Top Main Facet. The second averaged measurement is of a maximum of eight measurements from the Table to the center point of the Bottom Main Facets at the Girdle. The average of these two distances establishes the Center of Girdle Line, or the center of the Girdle of the diamond. The Center of Girdle Line Deduction Rule of the invention is then used to assess such measurements (Step 112). If the Center of Girdle Line cannot be established under all eight main facets, meaning basically that a straight line around the perimeter of the Girdle cannot be drawn, the diamond is determined not to have a Table that is parallel to the Girdle and is accorded a failure grade (Step 114). As such, no further measurements of the stone are necessary. If a Center of Girdle Line is established, the next step 116 is to measure the Bottom Main Facets as described below.

Bottom Main Facets

Assuming the Center of Girdle Line can be established, next each of the eight Bottom Main Facets of the diamond is measured (Step 116). Measurements should be at least to the nearest 1/10th of a degree. In the first embodiment, the angle, straightness, and depth of each Bottom Main Facet is measured. Such data is then analyzed individually and points are deducted for deviations from a desired or optimal measurement according to the Bottom Main Facet Deduction Rules (Step 118). Although not reflected in FIG. 2, each rule is preferably, although not necessarily, applied immediately after the particular angle, straightness and depth measurements are made.

In first measuring the angle of the Bottom Main Facets, the ideal or critical angle for such facets is 40.75 degrees. FIG. 8 illustrates the Deduction Point Value Lookup Table, which is based on the Bottom Main Facet Angle Deduction Rule. According to the Rule, if the angle of the Bottom Main Facet is within 0.05 degrees of the critical angle of 40.75 degrees, no point deduction is taken; if the angle of the Bottom Main Facet is 0.05 degrees above or below 40.75 degrees, 2 (two) points are deducted; then, for every additional 1/10th of a degree the angle of the Bottom Main Facet is over or under 40.75 degrees, 2 (two) additional points will be deducted. For example, referring again to Table 1, if the angle of a Bottom Main Facet is measured at either 40.1 degrees or 41.4 degrees, a total of 14 (fourteen) points will be deducted. In addition, the Bottom Main Facet Angle Deduction Rule states that stones having bottom facet angle measurements less than 38.4 degrees or greater than 45.7 degrees are considered unsuitable for scoring and are rejected.

Next, assuming the angles of the Bottom Main Facets are such that the stone is suitable for scoring, the Bottom Main Facets are measured for a deviation of straightness. According to the method of the presently described embodiment, four Bottom Main Facets are measured for straightness, each of which is measured six different ways. In addition, the first Bottom Main Facet to be measured for straightness should be the one, or one of those, having an angle measurement closest to 40.75 degrees, while the other three Bottom Main Facets to be measured for a deviation of straightness should then be the next three from the first measured Bottom Main Facet in a clockwise direction.

According to the inventor's system and method, each of the four chosen Bottom Main Facets will be measured for a deviation from straightness with respect to:

(a) The Bottom Main Facet that is 180 degrees opposite the facet being measured;
(b) The Main Facet directly on top of the Bottom Main Facet being measured;
(c) The neighboring Bottom Main Facet that is situated 90 degrees clockwise to the facet being measured;
(d) The neighboring Bottom Main Facet that is situated 90 degrees counter-clockwise to the facet being measured;
(e) The direct neighboring facet 45 degrees clockwise to the facet being measured; and
(f) The direct neighboring facet 45 degrees counter-clockwise to the facet being measured.

The result of such measurements is the twist difference between the facets, sometimes called the "twist results." The twist difference between the facet being measured and the Bottom Main Facet 180 degrees opposite such facet is termed "Twist 180." The twist difference between the facet being measured and Main Facet directly on top of such facet is termed "Twist Above/Below." The twist difference between the twist readings of the facet being measured and the Bottom Main Facet approximately 90 degrees clockwise from it is termed "Twist 90c." The twist difference between the facet being measured and the Bottom Main Facet approximately 90 degrees counter-clockwise from it is termed "Twist 90CC." The twist difference between the facet being measured and the direct neighboring facet 45 degrees clockwise from it is termed "Twist 45C," while the twist measurement between the facet being measured and the next main facet counter-clockwise from it is termed "Twist 45CC."

As indicated above, after the deviation from straightness of the first Bottom Main Facet is measured, the remaining three Bottom Main Facets in clockwise order from the first facet are measured for straightness. Then, the Bottom Main Facet Straightness Deduction Rule is used to assess such "twist results." According to the Rule, 1 (one) point is deducted for the first 1/2 degree of twist, or out of twist, from each of the facets in the six above-described measurements. Then, for every additional 1/2 degree out of twist after that, 2 (two) more points are deducted.

According to the presently described method of the invention, next the depth of each Bottom Main Facet is measured. Such depth is measured in relation to the Center of Girdle Line of the stone as calculated above. Ideally, the depth of a Bottom Main Facet should be 1.1% above the Center of Girdle Line. The depth of each Bottom Main Facet is therefore measured to determine its deviation above or below this value, after which the Bottom Main Facet Depth Deduction Rule is applied. According to the Rule, 1 (one) point is deducted for every 1/2% that the depth is greater than 1.1% above the Center of Girdle Line, and 2 (two) points are deducted for every 1/2% that the depth is below 1.1% of the Center of Girdle Line.

Top or Crown Main Facets

After the angle, straightness, and depth of the Bottom Main Facets has been measured, the angle, straightness, and depth of the Top or Crown Main Facets is measured (Step 120) in a generally similar manner, after which the Crown Main Facet Deduction Rules are individually applied after each measurement (Step 122). First, the angle of each of the eight Top Main Facets is measured to at least the nearest ¹⁄₁₀th of a degree. The ideal or critical angle for the Top or Crown Main Facets is 34.5 degrees. FIG. 9 illustrates the Crown Main Facet Angle Lookup Table having the deduction point values for the Top Main Facet angles, and which deduction point values are based on the Top or Crown Main Facet Angle Deduction Rule. According to the Rule, 1 (one) point is deducted for every ¹⁄₁₀th of a degree the angle of a Top Main Facet is over or under 34.5 degrees. For example, referring still to FIG. 9, if the angle of a Top or Crown Main Facet is measured at either 33.3 degrees or 35.7 degrees, 12 points will be deducted from the total score.

Next, four of the Top Main Facets are measured for a deviation of straightness or twist with respect to neighboring facets. The first Top Main Facet to be measured for a deviation of straightness should be the one, or one of those, having an angle measurement closest to 34.5 degrees. The other three Top Main Facets to be measured for a deviation of straightness should then be the next three Top Main Facets from the first measured Top Main Facet in a clockwise direction.

Each Top or Crown Main Facet to be measured for a deviation from straightness is measured with respect to:

(a) The Top Main Facet that is 180 degrees opposite the facet being measured (Top Twist 180);
(b) The Main Facet directly below or on the bottom of the facet being measured (Twist above/below);
(c) The neighboring Top Main Facet that is situated 90 degrees clockwise to the facet being measured (Twist 90c);
(d) The neighboring Top Main Facet that is situated 90 degrees counter-clockwise to the facet being measured (Twist 90cc);
(e) The direct neighboring facet on top that is 45 degrees clockwise to the facet being measured (Twist 45c); and The direct neighboring facet on top that is 45 degrees counter-clockwise to the facet being measured (Twist 45cc).

After the deviation from straightness of the first Top or Crown Main Facet is measured, the straightness of the three Top Main Facets in clockwise order from the first facet is measured. Then, such "twist results" are assessed using the Top or Crown Main Facet Straightness Deduction Rule. According to the Rule, 1 (one) point is deducted for the first ½ degree of twist, or out of twist, from each of the facets described above. Then, for every additional ½ degree out of twist after that, 2 (two) more points are deducted.

Next, the depth of the Top Main Facets is measured. Such depth is measured in relation to the Center of Girdle Line of the stone as calculated above. Ideally, the depth of a Top Main Facet should be 1.1% above the Center of Girdle Line. The depth of each Top Main Facet is therefore measured to determine its deviation above or below this value, after which the Top or Crown Main Facet Depth Deduction Rule is applied. According to the Rule, 1 (one) point is deducted for every ½% that the depth is greater than 1.1% above the Center of Girdle Line, and 2 (two) points are deducted for every ½% that the depth is below 1.1% the Center of Girdle Line.

Bottom Brilliandeering Facets—(Bottom Halves)

After the Top or Crown Main Facets have been measured, the Bottom Brilliandeering Facets must be measured (Step 124). Similar to the Main Facets, the Brilliandeering Facets are measured for proper angle, straightness, and depth. One method is to measure the height of the Bottom Brilliandeering Facets as a percentage of the Main Facet on which it is cut. Alternatively, the actual angle of the Brilliandeering Facets could be measured and used. After the angle, straightness, and depth measurements are taken, such measurements are assessed using the Bottom Brilliandeering Facet Deduction Rules (Step 126). According to the preferred method of the invention, the Bottom Brilliandeering Facets are measured for height in relationship to the Main Facet such Brilliandeering Facet is cut on. Then, according to the inventor's Bottom Brilliandeering Facet Angle Deduction Rule, if the height of a Bottom Brilliandeering Facet is 73–77% of the height of the Main Facet it is cut on, 0 (zero) points are deducted; if the height of the Bottom Brilliandeering Facet is 70–72% or 78–80% of the height of its Main Facet, 2 (two) points are deducted, while if the height of the bottom brilliandeering facet is greater than 80% or less than 70% of the height of its Main Facet, 5 (five) points are deducted.

As an alternative, instead of measuring the heights of the Bottom Brilliandeering Facets, the actual angles of such facets can be measured. Such measurement is then compared with the angle of the Bottom Main Facet on which such Bottom Brilliandeering Facet is located. Ideally each Bottom Brilliandeering Facet should be 1.75–2.5 degrees higher than the Bottom Main Facet on which it is cut. According to the Deduction Rule, therefore, 0 (zero) points will be deducted if a Bottom Brilliandeering Facet is 1.75–2.5 degrees higher than the Bottom Main Facet on which it is situated; and ½ (one-half) point will be deducted for every ¹⁄₁₀th of a degree that the Bottom Brilliandeering Facet is in excess of 2.5 degrees higher than its Main Facet, or for every ¹⁄₁₀th of a degree that the Bottom Brilliandeering Facet is under 1.75 degrees higher than the main facet measurement of the bottom main angle.

The straightness of the Bottom Brilliandeering Facets is also measured by recording the amount of twist with respect to its adjacent or matching Top Brilliandeering Facet. Such facets may also be thought of as a top half and bottom half of the same facet, with the top half being on the Crown of the diamond and the bottom half on the Pavilion. Therefore, the twist between the top half and bottom half is measured. The amount of twist is normally measured by the amount of twist by an edge measurement at two points of the half. Such points are at the center point on the main facet where it touches its immediate neighboring half, and under the rib line. The straightness rule for such facets is termed the Bottom Halves/Top Halves Straightness Deduction Rule. According to the Rule, ½ (one-half) point is deducted for each 0.1% of deviation left or right from each of the two measuring points on each of the 16 Brilliandeering Facets, for a total of 32 measuring points.

The depth of each Bottom Brilliandeering or Lower Girdle Facet is also measured. Such measurements are taken under the rib line and should be 1.1% greater than the Center of Girdle Line of the area of the diamond it is on. In addition, the depth should equal the depth of the Main Facet it is on. According to the inventor's Bottom Brilliandeering Depth Deduction Rule, 1 (one) point is deducted for each ½% that the depth of a Bottom Brilliandeering Facet is above the related main facet depth measurement. In addition, either 2 (two) points are deducted for each ½% that the depth measurement is below the related main facet depth measurement, or 5 (five) points are deducted if the half-depth of the Bottom Brilliandeering Facet is below the Center of Girdle Line.

Top Brilliandeering or Upper Girdle Facets

The Top Brilliandeering or Upper Girdle Facets, or as also described above the top half brilliandeering facets, are also measured (Step 128) for proper angle, straightness, and depth. Similar to the measurement of the angle of the bottom halves, the height of each Top Brilliandeering Facet is preferably measured as a percentage of the main facet on which it is cut. Alternatively, the actual angle of the Brilliandeering Facets could be measured and used. The Top Brilliandeering Facet Reduction Rules are applied after each set of measurements is taken (Step 130).

Accordingly, in the preferred arrangement, the height of each Top Brilliandeering Facet is measured in relation to the main facet it is on. According to the inventor's Top Brilliandeering Facet Deduction Rule, if the height of a Top Brilliandeering Facet is 73–77% of the height of its main facet, 0 (zero) points are deducted; if the height of a Top Brilliandeering Facet is 70–72% or 78–80% of the height of its main facet, 3 (three) points are deducted; and if the height of the Top Brilliandeering Facet is greater than 80% or less than 70% of the height of its main facet, 8 points are deducted. As an alternative, instead of measuring the heights of the Top Brilliandeering Facets, the actual angle of such facets may be measured. Ideally, the Top Brilliandeering Facets should be 6 degrees higher than the Bottom Main Facet that they are on. According to the inventor's Top Brilliandeering Facet Deduction Rule, ½(one-half) point is deducted for every ¹⁄₁₀th of a degree the Top Brilliandeering Facet is higher than 6 degrees greater than the main facet, and ½ (one-half) point is deducted for ¹⁄₁₀th of a degree the Top Brilliandeering Facet is under 5.75 degrees greater than the main facet measurement of the bottom main angle.

The straightness of the Top Brilliandeering Facets is also measured. The Top Brilliandeering Facet Deduction Rule is part of the Bottom Halves/Top Halves Straightness Deduction Rule discussed with respect to the straightness of the Bottom Brilliandeering Facets above. According to the Rule, ½ (one-half) point is deducted for each 0.1% of deviation left or right from each of the two measuring points on each of the 16 Brilliandeering Facets, for a total of 32 Brilliandeering Facet measuring points.

According to the invention, the depth of the Top Brilliandeering facets is also measured. Such depth is measured in the same manner in which the Bottom Brilliandeering Facets are measured as discussed above, i.e. under the rib line and in relation to the Center of Girdle Line of the stone. Ideally, the depth should be 1.1% greater that the Center of Girdle Line of that particular area of the diamond, and in addition should be equal to the depth of the main facet the Top Brilliandeering Facet is on. Each of the top main facets is therefore measured to determine its deviation above or below 1.1% greater than the Center of Girdle Line. According to the Top Brilliandeering Facet Depth Deduction Rule, 1 (one) point is deducted for each ½% the Top Brilliandeering Facet is greater than 1.1% above the Center of Girdle Line. In addition, either 2 (two) points are deducted for each ½% below 1.1% above the Center of Girdle Line, or 5 (five) point are deducted if the depth of the Top Half Brilliandeering Facet is below the Center of Girdle Line.

Star Facets

The straightness and angle of each of the Star Facets of the stone is also measured and accounted for in the first preferred embodiment of the inventor's cut grading system and method stone. With respect to straightness, ideally, each Star Facet, which facets are located above and between the Top Main Facets of the stone around the Table, should be at 22.5 degrees measured from the angle of either Top Main Facet situated either to the left or right of such Star Facet. The straightness of all remaining Star Facets should be measured from the main angle in the same direction.

After such straightness measurements have been taken, the inventor's Star Facet Straightness Deduction Rule is applied (Step 134) to the measurements. According to the Rule, ½ (one-half) point is deducted for each 0.1% of deviation from the ideal angle of 22.5 degrees off the main facet. Thus, if the Star Facet is positioned at 22.8 degrees, 1½ points will be deducted according to the Rule.

The angle of the Star Facets is determined by measuring the distance from the point of the Star where it meets the rib line of the Top Brilliandeering Facets to the Table from a point on the Main Facet directly under the Star Facet junction and over the Top Brilliandeering Facet junction when that point is on a parallel line to the Table of the diamond. Such measurement is already taken by default when the Top Brilliandeering Facets are measured as discussed above, so any deductions are effectively taken into consideration at such time. In addition, deductions are also taken into consideration at the time also by the Top Brilliandeering Facet Angle Deduction Rule, since according to such Rule the deductions are 50 percent greater than the deductions according to the Bottom Brilliandeering Facet Angle Deduction Rule.

Roundness

Another factor considered in scoring the quality of the cut of a round brilliant diamond according to the present system is the overall roundness of the diamond. To measure roundness (Step 136), a total of eight measurements must be taken of the diameter of the diamond measured under the main facets and under the ribline of each set of top and bottom brilliandeering facet halves. According to the Roundness Deduction Rule (Step 138), 0 (zero) points are deducted if any one of the eight measurements is 1% or less than the maximum measurement point; and for every additional 0.5% discrepancy greater than a 1% discrepancy, an additional 10 points is deducted. The maximum measurement point is the maximum measured diameter of a particular diamond.

Table

The Table of the diamond may also optionally be measured (Step 140) and included in the scoring of the cut of the diamond. The Table should be measured as a percentage of the diameter of the diamond in four places, each at the midpoint of where the Star Facets meet in the center of each Main Facet.

Ideally, according to the Table Deduction Rule of the presently described embodiment of the invention, the diameter of the Table as a percentage of the diameter of the stone should be between 53%–57%. According to the Table Deduction Rule (Step 142), 10 (ten) points are deducted for each percentage point greater than 57%, while 25 (twenty-five) points are deducted for each percentage point less than 53%. In addition, 5 (five) points are deducted for each percent of deviation.

Moderator Factor

To ease the transition from scoring diamonds with the abbreviated method described below to scoring diamonds with the full method and system just described, the deductions total as dictated by the inventor's Deduction Rules may be adjusted 40 to 70 percent. A typical moderator will be 50%. Such modification maintains the integrity of the relationships between the facets and facilitates changes to scoring software. In other words, the moderator adjusts for the number of measurements taken and resulting deductions, which will be greater in the full scale system than in the abbreviated system, so that there is unity between the scores.

While one preferred system and method for calculating a comprehensive score indicative of the overall quality of the cut of a brilliant round diamond has been described in detail above, it should be evident that more, less, or slightly alternative measurements could be taken while staying true to the basic concept and nature of the invention. In addition, the Deduction Rules may be adjusted slightly, for example, to accommodate slightly more or less precise measurements or future scanning and measuring technology. While the first described embodiment is based on measurements taken using full capability technology, the embodiment described below is based on existing measuring technology using the Sarin DiaScan machine. Such machine is sufficiently precise to give measurements of up to ±0.2 degrees, and measurements are obtained from the Sarin DiaScan machine MNF report that supplies a variety of measured values for each diamond that is measured using the machine. As in the previous embodiment, each diamond starts with a perfect score of preferably 1000 and point values are assigned for deviations from the various desirable measurements according to the inventor's Deduction Rules. The deductions are then summed up and subtracted from the perfect score value, resulting in a score that is indicative of the quality of the cut of the stone.

Figure 3:
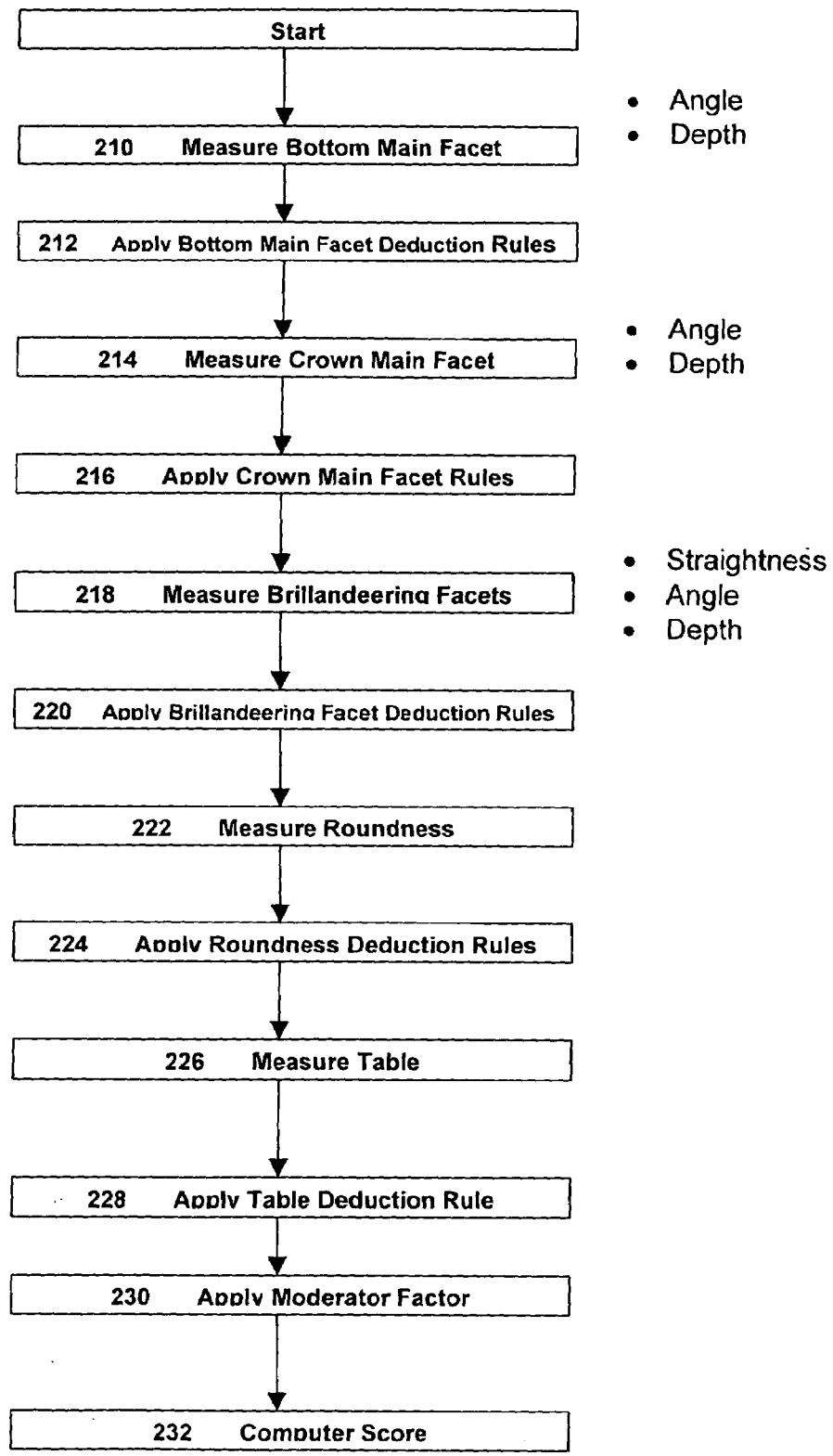
FIG. 3 is a flow chart of steps in measuring and assessing the quality of the cut of a diamond in the second described embodiment of the invention.

In the arrangement described below, the shape/angle and depth of the Bottom Main Facet and Top or Crown Main Facet are measured, and the straightness, angle, and depth of the Bottom and Top Brilliandeering Facets are measured and evaluated. Such measurements are limited to the capabilities of the Sarin DiaScan machine or a similar model. Also measured and evaluated are the "out of roundness" and Table size of the diamond. FIG. 3 is a flow chart wherein the major steps of the second preferred embodiment of the invention are outlined.

Bottom Main (Pavilion) Facets

In the presently described embodiment of the invention, as indicated above, first the angle and depth of the eight Bottom Main Facets are measured (Step 210), and then the Bottom Main Facet Deduction Rules are applied (Step 212). Measurements should be at least to the nearest 1/10th of a degree. The ideal or critical angle for the Bottom Main Facets is 40.75 degrees. Bottom Main Facet angle measurement data is taken from the Sarin report readout, where it is typically listed in the column entitled "Pav°" which stands for "Pavilion Degrees."

Referring again to FIG. 8 there is illustrated the point deduction values for deviations from the ideal angle of 40.75 degrees of the Bottom Main Facets. The point deduction values are based on the inventor's Bottom Main Facet Angle Deduction Rule. According to the Rule, if the Bottom Main Facet angle is within 0.05 degrees of 40.75 degrees, 0 (zero) points are deducted. Then, for every additional 1/10th of a degree over or under 40.75 degrees, 2 (two) more points are deducted. However, if the measured angle of a Bottom Main Facet is less than 38.4 degrees or greater than 45.7 degrees, the stone is rejected completely as being of such low quality that it is unsuitable for scoring.

Next, the depth of the Bottom Main Facets is measured in relation to the Center of Girdle Line of the stone. Such depth should be 1.1% above the Center of Girdle Line. When combined with the depth of the Crown Main Facet depth directly above the Bottom Main Facet being measured, the desired total width or thickness of the Girdle should be 2.2%. The thickness of the Girdle is measured by the Sarin DiaScan machine and is listed on the DiaScan report as G.Bzl %. The G.Bzl % measurement is assessed using the Bottom Main Facet Depth Deduction Rule. FIG. 10 illustrates the full G.Bzl Deduction Lookup Table according to the Rule, while Table 11a below is a simplified form of FIG. 10. Point value deductions are assigned according to such Tables.

TABLE 10a

| G. Bzl % | Deduction |
|---|---|
| 0–1.7% | 4 pts. |
| 1.8–2.6 | 0 pts. |
| 2.7–3.2 | 4 pts. |
| 3.3–3.7 | 6 pts. |
| 3.8–4.2 | 8 pts. |
| 4.3–4.7 | 10 pts. |
| 4.8–5.2 | 12 pts. |
| 5.3–5.7 | 14 pts. |
| 5.8–6.2 | 16 pts. |
| 6.3–6.5 | 18 pts. |

Top (Crown) Main Facets

The angle and depth of the eight Top or Crown Main Facets is also measured (Step 214), also to the nearest 1/10th of a degree, after which the Crown Main Facet Deduction Rules are applied (Step 216).

Starting with the angle of the Top Main Facets, the ideal or critical angle for such facets is 34.5 degrees. Such information is listed on the Sarin DiaScan report as "Crown Deg." Referring again to FIG. 9, there is illustrated the deduction point values for the angle of the Top Main Facets. According to the Crown Main Facet Angle Deduction Rule, for every 1/10th of a degree the Main Facet Angle is over or under 34.5 degrees, 1 (one) point will be deducted. If the measured Crown Main Facet angle is less than 29 degrees or greater than 39.9 degrees, the stone will be rejected as being unsuitable for scoring.

The depth of the Top or Crown Main Facets is also measured and point value deductions taken following the Crown Main Facet Depth Deduction Rule. As discussed above with reference to the depth of the Bottom Main Facets above, such depth is measured in relation to the Center of Girdle Line of the stone, and should be 1.1% above the Center of Girdle Line. Such measurement is a combined measurement in that it is combined with the depth of the Bottom Main Facet directly below the Crown Main Facet, so that the ideal width of the Girdle is 2.2%.

As indicated above, the readings used are taken from the Sarin Diascan report where they are listed under the heading G.Bzl %. The G.Bzl % measurement is then assessed using the Main Facet Depth Deduction Rule point deductions, which have already been discussed and are listed in Tables 4 and 5.

Brilliandeering Facets—Bottom and Top Halves

After the angle and depth of the Main Facets has been measured and assessed, the straightness, angle, and depth of the Bottom and Top Brilliandeering Facets must be measured (Step 218) and assessed through application of the Brilliandeering Facet Deduction Rules.

First, the straightness of adjacent pair of Bottom and Top Brilliandeering facets is measured. The straightness measurements are termed the "twist result" and taken from the "Twist Deg" column of the Diascan report. The "twist result" represents the straightness of adjacent Top and Bottom Brilliandeering Facets at the midpoint located in the center of the main facet.

According to the inventor's Bottom/Top Brilliandeering Facet Straightness Deduction Rule, 7 (seven) points are deducted for each degree of deviation greater than zero. FIG. 11 illustrates the Twist Degree Lookup Table following the Bottom/Top Brilliandeering Facet Straightness Deduction Rule. Thus, for example, if the Twist Deg reading is 0.4, no points are deducted, but if the reading is 4.0, twenty-eight points are deducted.

The angle of the Bottom and Top Brilliandeering Facets is also measured and assessed in the inventor's cut scoring system and method. Such measurement appears as "G.hlv %" on the DiaScan report, referring to the Girdle halve ribline. The G.hlv % measurement is particularly important since is could be an indication of the depth and/or straightness of adjacent Top and Bottom Brilliandeering Facets.

FIG. 12 illustrates the G.hlv% Deduction Lookup Table following the Bottom/Top Brilliandeering Facet Angle Deduction Rule, while Table 12a illustrates a simplified G.hlv % Deduction Table according to such Rule.

TABLE 12a

| G. Hlv % | Deduction |
| --- | --- |
| 0–1.7% | 4 pts. |
| 1.8–2.6 | 0 pts. |
| 2.7–3.2 | 4 pts. |
| 3.3–3.7 | 6 pts. |
| 3.8–4.2 | 8 pts. |
| 4.3–4.7 | 10 pts. |
| 4.8–5.2 | 12 pts. |
| 5.3–5.7 | 14 pts. |
| 5.8–6.2 | 16 pts. |
| 6.3–6.7 | 18 pts. |

If the measured G.hlv % is greater that 6.7, the stone should be rejected as being unsuitable for scoring.

Next, the depth of the Bottom and Top Brilliandeering Facets is measured. The depth should leave a desired girdle thickness, listed as "G.min %" on the DiaScan report, of roughly 0.33 percent of the thickness of the girdle under the main facets (G.bzl %) and halve ribline (G.hlv %). Sixteen "G.min" measurements are taken, one for each Bottom and Top Half Brilliandeering Facet. Zero is a valid measuring value. Point deductions are taken based on the Bottom/Top Brilliandeering Facet Depth Deduction Rule.

FIG. 13 illustrates the G.min% Deduction Lookup Table based on such rule, while Table 13a illustrates a simplified table of deductions according to the Rule.

TABLE 13a

| G. min % | Deduction |
| --- | --- |
| <.5 | 4 pts. |
| 0.5–0.7 | 0 pts. |
| 0.7–1.1 | 0 pts. |
| 1.2–2.2 | 2 pts. |
| 2.3–3.3 | 4 pts. |
| 3.4–4.4 | 6 pts. |
| 4.5–6.5 | 8 pts. |
| 6.6–8.6 | 10 pts. |

Roundness

In addition to measuring the facets of the diamond, the roundness of the diamond is also measured (Step 222) and assessed using the Roundness Deduction Rules (Step 224). Roundness is assessed by measuring the diameter of the stone under the Main Facets, giving a total of eight measurements. The difference between the maximum diameter and minimum diameter is then calculated as a percentage.

Again, in the presently described embodiment such measurement is taken from the Sarin DiaScan report, where it is listed as "Diameter." According to the Roundness Deduction Rule, 0 (zero) points are deducted if the resulting measurement is 1% or less than the maximum measurement point, and 10 (ten) points are deducted for each 0.5% greater than a 1% discrepancy.

Table

The Table of the diamond is also measured (Step 226) and assessed using the Table Deduction Rules (Step 228), with the Table being measured by the DiaScan machine as a percentage of the diameter of the diamond. Such measurement is taken in four places on the diamond, and is listed on the DiaScan Report as "Table %".

According to the inventor's Table Deduction Rule, 5 (five) points are deducted for each percentage point the Table % measurement is greater than 57%, and 25 (twenty-five) points are deducted for each percentage point the Table % measurement is less than 53%.

Moderator Factor

After the measurements have been taken and assessed using the Deduction Rules of the inventor's system and method, the points deducted according to each Rule are summed and then subtracted from 1000, resulting in a cut quality score for the diamond. To ease the transition from scoring diamonds using the just-discussed abbreviated method to scoring diamonds with the previously discussed full capability technology method, the total deductions may be adjusted using a moderator factor (Step 230). Such factor may adjust the deductions total by between 40 and 70%. Applying the moderator factor to an overall moderation helps maintain the integrity of the relationships between the facets and facilitates changes to the scoring software. After the moderator is applied, the final score may be calculated (Step 232).

FIG. 4 illustrates sample input data from a DiaScan report, with the name of the cut or feature being measured listed in the first column of the table, and with the various measured results listed in the remaining columns. FIG. 5 illustrates a sample deduction table, with the resulting deductions being assessed according to the inventor's Deduction Rules as described above, and according to the measurements or input data in FIG. 4. For each measurement shown in the columns of FIG. 4, a corresponding point value deduction is listed in the similar columns of FIG. 5. The last column of FIG. 5 provides a total for the point deductions for each particular measurement, while below the sum of such deductions for all of the columns and measurements is provided. The next row indicates the total deduction after the moderator factor has been applied, which in this case is 50%. Finally, the "BrayScore" is the final score of the quality of the cut of the diamond, with the moderator total deduction being subtracted from a base or perfect score of 1000.

Figure 6:
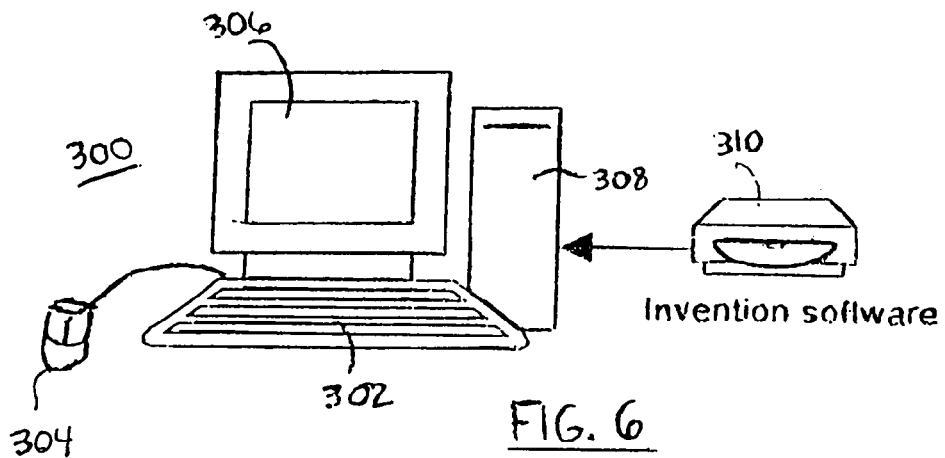
FIG. 6 is a schematic diagram showing a suitable computer equipment in which the computer software of the present invention may be used.

As indicated above, the present diamond cut quality scoring system and method is preferably implemented using a software program which will calculate a score based on the measurements input into the program. The program can take a number of forms which are well known in the art, such as by utilizing Microsoft Excel, SQL, or other common programming languages, or by a standalone program. FIG. 6 depicts a microprocessor-based desk top computer station 300 including a keyboard 302, a mouse or other compatible pointing device 304, a graphics display monitor 306, and computer 308. A CD-ROM drive 310 is shown as the storage medium for the invention diamond cut scoring software to be utilized on computer 308 to perform the present invention. However, any data storage medium compatible with the computer, or the computer itself, may be used. Other peripheral equipment such as a printer may be also be included. Computer 308 should have a 500 MHz or higher processor, preferably including at least Windows version 98 or XP or higher. In addition, at least 64 MB of RAM or higher is preferred, although not necessarily required unless in a Windows 2000 environment. Computer 308 may also be pre-loaded with suitable software such as Microsoft Excel, Access, or SQL or similarly sophisticated programs. A sufficient amount of hard-disk space, preferably at least 50 MB should be available for storing the invention software. Other operating systems such as Macintosh or Linux may also be used. The software program may also be incorporated directly into the software used by the electronic measuring machine, such as the Sarin Diascan machine. The interaction of such software program and the sending and receiving of information between the software and either Web servers or other programs is well known to those of ordinary skill in the art. Upon new diamond cut measurement data being input into the program, the program will access stored reference measurements as well as the Deduction Rules of the invention described above. The program may then compare the stored reference data with the new measurements. Once all of the required measurements and information has been received by the program, the program would then compute the cut score for each diamond based upon the Deduction Rules used in the scoring system described above. The moderator factor may also be used to normalize the score, thereby producing a normalized final score.

Figure 7:
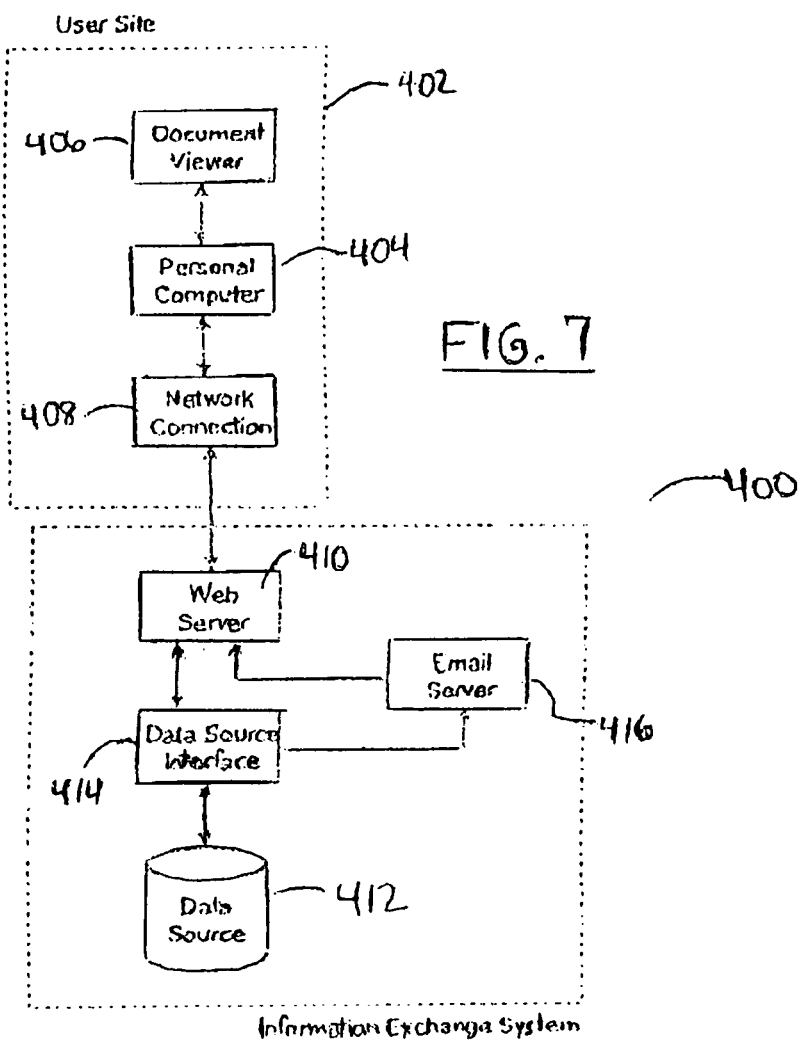
FIG. 7 is a block diagram illustrating a typical arrangement for use of the present invention system and software via the Internet.

It is also contemplated that customers will be able to obtain diamond cut scores over a computer network such as the Internet. FIG. 7 is a block diagram illustrating a typical information exchange system arrangement 400 for use with the system and method via a computer network. User site 402 may include a personal computer 404 equipped with a document viewer 406 such as a video monitor and a network connection 408. Because of the vastness of the Internet "network of networks," which connects a large number of computer networks and sub-networks to each other through several regional backbone systems around the world, and the usability of one portion of the Internet in particular, the World Wide Web ("Web"), where organizations routinely conduct business, the Web is a convenient means for enabling users to obtain diamond cut quality scores according to the teachings of the invention and using a graphical user interface "GUI" such as a web browser, which is software application that allows users to access and view electronic documents in a browser window. Users would locate the inventor's web site via a web server 410 and login using a username and a password after registering and for a preferably for a fee input the applicable measurements of the cut of a brilliant cut diamond. The system software (data source 412), likely stored on a server to facilitate access and use, is accessed via data source interface 414, after which the data is processed and a cut score is calculated in accordance with the Deduction Rules and other teachings of the invention. The data may be converted into a web document using Hypertext Markup Language ("HTML") and forwarded to the user via the Internet. Alternatively, the results may be forwarded using e-mail via e-mail server 416. To enhance security, the server may use Secure Socket Layer ("SSL") technology, which is widely known by those skilled in the art and is integrated into most commercially acceptable web browsers. The Internet may also be used to allow a person purchasing a diamond already having a score calculated using the system of the invention to verify the legitimacy of the score. To accomplish this, a control number is issued with each score which may be input into the web screen, wherein the database of the software will access the true score. If the control number and score do not match, the score is to be considered invalid.

The scoring system of the invention as just described is designed particularly for use in assigning a score to the quality of the cut of a modern round or brilliant cut diamond. However, it should be evident that such basic scoring system could also be adjusted so that is may be applied to calculate a cut score for other shapes of diamonds, some of the more commonly known are marquise, heart, princess/radiant, emerald, and trillion. The system may also be adjusted to be applied to other fancy-shaped diamonds or other stones if desired, although of course different measurements and criteria likely would be considered in determining the quality of cut of such stones.

The potential and actual benefits of the present system and method are numerous. Diamond dealers will benefit from using a quicker, more accurate, and objective system whereby a seller can describe the make on a diamond more particularly using the resulting cut quality score. This in turn will boost the trust and confidence of both the buyer and the seller, and will reduce memo returns. In addition, dealers will benefit from the fact that value will be added to lower quality stones having a score or rating, which stones currently usually are not provided with grading reports. Value will also be added to premium cut stones, since the present system will identify minute differences between similarly cut stones and differentiate actual premium stones from good quality but not quite premium quality stones. Finally, cutters who know that the quality of their work has been graded and converted into a form wherein cutting errors are easily identified will have a further incentive to do better work, and those cutter's who do better work will benefit from the ability to command higher labor prices.

Retail stores may also benefit from use of the inventor's system and method. In addition to boosting the trust and confidence between buyers and sellers, a retail store owner can use the system to assess the quality of a cut when buying inventory. In addition, once lay purchasers of diamonds are exposed to and become familiar with the system, it is very likely to be quickly accepted and approved. While random casual testing has resulted in an almost 100% approval rating for the system, it should be evident that such system makes it much easier for consumers to compare and identify differences between the cut of two diamonds, making it less likely that they will make a poor buying decision. The system is also easily understood and explained to potential purchasers, and adds to the conciseness and accuracy of the color grading and clarity grading systems now used. In addition, just as today a diamond having a large carat weight is a source of pride to the owner, a diamond having a high numerical score or rating may also become a source of pride of ownership and exclusivity for the owner.

Gem laboratories adopting the present system will be able to increase their revenue from the price charge for issuing a grading report, with the system adding significant value to such reports. In addition, as indicated above, while due mostly due to lack of knowledge, consumers are most interested in the clarity and carat weight of a stone. The present system will make it easier for consumers and professionals alike to evaluate and consider the cut of a stone in evaluating a stone. No additional personnel are required to perform the grading using the present inventor's system, since the software platform may automatically calculate such information. As indicated above, more lower quality stones will also eventually be rated.

Manufacturers will also benefit from the present system, primarily due to the creation of a secondary market for lower clarity and quality stones that usually do not command grading reports. Cutters with the most skill will also be easily identified and will benefit from such recognition. In addition, manufacturers that are not known for manufacturing quality stones may benefit from receiving high grades for their premium stones. Manufacturers using the invention can also now improve the cut of a stone or stone prior to grading and the like, thereby causing cutters to improve their work. Finally, current price guides and sheets, which are filled with ambiguous discounts to provide fungability and accuracy in describing make and can easily be adapted to current pricing sheets adding accuracy to the pricing of diamonds. Other benefits may also come to light in the future.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

I claim:

1. A method of classifying gemstones comprising:
   (a) mounting the gemstone upon a suitable support;
   (b) directing electromagnetic waves of a limited wavelength at said gemstone,
   (c) measuring the reflected electromagnetic waves in a manner such that the characteristics of the reflected electromagnetic radiation from individual facets of said gemstone are isolated and measured to represent the important reflectance characteristics of said facets,
   (d) comparing each facet as measured with the facets of a theoretically perfect gem of the same character and subtracting from a theoretically perfect score of a predetermined number of points a preselected number of points dependent upon the variance of the actual facts with the theoretical facets, and
   (e) at the completion adding up the remaining points for each facet and using the number as a sum of the value of the gem.

2. A method of classifying gemstones in accordance with claim 1 wherein the gemstone is a brilliant cut diamond and the measurements are applied to the bottom main facet, the crown main facet, the brilliandeering facets and the roundness of the diamond.

3. A method of classifying gemstones in accordance with claim 2 wherein the angle and depth of the bottom of the bottom main facet, the crown main facet, and brilliandeering facets are measured as well as the straightness of the brilliandeering facets.

4. A method of classifying gemstones in accordance with claim 3 wherein the measurements begin with an attempt to measure the center of the girdle line and if successful the straightness of the main bottom and top main facets are also measured and angle and straightness of the star facets are also measured.

5. A method in accordance with claim 4 wherein the initial numerical score is one thousand and measured deviations from the various elements are subtracted from such initial numerical score.

6. A method in accordance to claim 5 in which a predetermined moderating quantity is added to the score to make the same determination with fewer criteria compatible with the score using additional criteria.

7. An arrangement for determining the grade of a gemstone with multiple cut facets comprising:
   (a) means for directing electromagnetic radiation at said gemstone positioned in a holder,
   (b) means for monitoring reflected electromagnetic radiation from said gemstone and separating it into reflectance from various individual facets of the gemstone,
   (c) means for comparing the reflected electromagnetic radiation reflectance from each measured facet with the reflectance from a theoretically perfectly cut gemstone,
   (d) means for assigning a predetermined numerical point score to the facet deviations measured between the theoretically perfectly cut gemstone and actual gemstone, and
   (e) means for subtracting the cumulative point score of deviations from a perfectly cut gemstone from an arbitrarily assigned total score for a perfectly cut gemstone.

8. An arrangement for determining the grade of a gemstone in accordance with claim 7 wherein the various means for directing, mounting and comparing electromagnetic reflections are arranged for handling a brilliant cut diamond and the measurements are applied by suitable means with respect to the bottom main facet, the crown main facet, the brilliandeering facets and the roundness of the diamond.

9. An arrangement for determining the grade of a gemstone in accordance with claim 8 wherein means for directing, mounting and comparing electromagnetic reflections are further arranged to measure the angle and depth of the bottom of the bottom main facet, the crown main facet, and brilliandeering facets as well as the straightness of the brilliandeering facets.

10. An arrangement for determining the grade of gemstone in accordance with claim 9 wherein suitable measurement apparatus is provided to begin measurement with an attempt to measure the center of the girdle line and if successful further apparatus is used to measure the straightness of the main bottom and top main facets and the angle and straightness of the star facets are also measured.

11. An arrangement for determining the grade of a gemstone in accordance with claim 10 wherein suitable means is provided to provide an initial numerical score of one thousand and various measured deviations from the theoretical perfect score are subtracted from such initial numerical score.

12. An arrangement for determining the grade of a gemstone in accordance with claim 7 in which means is provided for introducing a predetermined moderating quantity to the score to make the same determination with few criteria compatible with the score using additional criteria.

* * * * *